United States Patent [19]

Soled et al.

[11] Patent Number: 4,584,323

[45] Date of Patent: Apr. 22, 1986

[54] FISCHER-TROPSCH HYDROCARBON SYNTHESIS WITH COPPER PROMOTED IRON/COBALT SPINEL CATALYST

[75] Inventors: Stuart L. Soled, Pittstown; Rocco A. Fiato, Scotch Plains, both of N.J.

[73] Assignee: Exxon Research and Engineering Co., Florham Park, N.J.

[21] Appl. No.: 735,964

[22] Filed: May 20, 1985

Related U.S. Application Data

[63] Continuation-in-part of Ser. No. 561,192, Dec. 14, 1983, Pat. No. 4,544,671.

[51] Int. Cl.$^4$ .............................................. C07C 1/04
[52] U.S. Cl. .................................... 518/700; 518/713; 502/331

[58] Field of Search ................................. 518/700, 713

[56] References Cited

FOREIGN PATENT DOCUMENTS 3319254 11/1984 Fed. Rep. of Germany .

*Primary Examiner*—Howard T. Mars
*Attorney, Agent, or Firm*—Edward M. Corcoran

[57] ABSTRACT

Slurried, high surface area, copper promoted Fe-Co spinels which are fully reduced/carburized provide exceptionally high activity and selectivity in the conversion of $CO/H_2$ to alpha-olefins. These copper promoted iron-cobalt catalysts maintain good activity and selectivity under low pressure reaction conditions.

23 Claims, No Drawings

FISCHER-TROPSCH HYDROCARBON SYNTHESIS WITH COPPER PROMOTED IRON/COBALT SPINEL CATALYST

CROSS REFERENCE TO RELATED APPLICATIONS

This application is a continuation-in-part application of co-pending U.S. Ser. No. 561,192 filed on Dec. 14, 1983 now U.S. Pat. No., 4,544,671.

BACKGROUND OF THE INVENTION

1. Field of the Invention

This invention relates to high surface area, copper promoted iron-cobalt spinel Fischer-Tropsch catalysts, their preparation and use in Fischer-Tropsch slurry processes for selectively producing high amounts of $C_2$ to $C_{20}$ alpha-olefin materials.

2. Brief Description of the Prior Art

Methods for preparing low molecular weight olefins by Fischer-Tropsch processes using coprecipitated iron-based catalysts including cobalt as cocatalyst, are well-known in the art, as described, for example, in U.S. Pats. Nos. 2,850,515; 2,686,195; 2,662,090; and 2,735,862; Aiche 1981 Summer Nat'l Meeting Preprint No. 408, "The Synthesis of Light Hydrocarbons from CO and $H_2$ Mixtures over Selected Metal Catalysts" ACS 173rd Symposium, Fuel Division, New Orleans, March 1977; J. Catalysis 1981, No. 72(1), pp. 37–50; Adv. Chem. Sem. 1981, 194, 573–88; Physics Reports (Section C of Physics Letters) 12 No. 5 (1974) pp. 335–374; UK Patent Application No. 2050859A; J. Catalysis 72, 95–110 (1981); Gmelins Handbuch der Anorganische Chemie 8, Auflage (1959), pp 88–96; and Chem. Ing. Tech. 49 (1977) No. 6, pp. 463–468.

It is further known that high levels of cobalt in coprecipitated iron-cobalt alloy catalysts produce enhanced selectivity to olefinic products under certain process conditions, as described in Stud, Surf. Catal. 7, Pt/A, pp. 432 (1981).

Although the above-described prior art describes catalysts and processes displaying good fixed bed olefin synthesis activity, what is particularly desired are slurry catalysts which can preferably be completely pretreated in situ in the slurry liquid to yield the reduced, carbided active catalysts in the process displaying the combination of good $C_2$–$C_{20}$ olefin synthesis activity, low selectivity to methane, coupled with long-term activity maintenace which is essential for a successful commercial process. Particularly desired is where the catalyst precursor is the metal oxide spinel of the final catalyst composition.

It has been found that low surface area ironcobalt spinels having BET surface areas below 5 $m^2/g$ are not readily pretreated in situ in a Fischer-Tropsch slurry liquid under mild conditions to readily yield active catalysts for producing $C_2$–$C_{20}$ olefins.

The preparation of high surface metal oxides is described in the French article, "C. R. Acad. Sc. Paris", p268 (May 28, 1969) by P. Courte and B. Delmon. The article describes a process for producing high surface area metal oxides by evaporating to dryness aqueous solutions of the corresponding glycolic acid, lactic acid, malic or tartaric acid metal salts. One oxide that was prepared by their described method was $CoFe_2O_4$.

However, the above references do not describe or suggest the use of copper promoted single phase Fe:Co spinels having iron-cobalt atomic ratios of 4:1 or above or suggest their applicability in conducting or carrying out slurry-type Fischer-Tropsch processes.

SUMMARY OF THE INVENTION

The present invention relates to unsupported, copper promoted, high surface area, iron-cobalt spinels, their preparation and use as catalysts in Fischer-Tropsch hydrocarbon synthesis for selectively producing high amounts of $C_2$ to $C_{20}$ alpha-olefin hydrocarbons. Thus, in one embodiment of this invention, the catalysts of this invention will be used to synthesize hydrocarbons, including $C_2$ to $C_{20}$ alpha-olefin hydrocarbons, by contacting said catalyst, at elevated temperature, with a gaseous feed mixture of $H_2$ and CO for a time sufficient to convert at least a portion of said feed to said hydrocarbons. This reaction is preferably conducted in a slurry reactor. In a preferred embodiment, the catalyst will be further promoted with one or more alkali or alkaline metals of Group IA and IIA. It is particularly preferred that the additional promoter metal comprise a Group IA alkali metal, such as potassium.

The high surface area iron-cobalt spinels can be prepared by a process of adding an alpha-hydroxy aliphatic carboxylic acid, e.g., glycolic acid, to an aqueous solution containing dissolved iron and cobalt salts and subsequently evaporating the solution to dryness to yield an amorphous mixed metal precursor salt. The so-formed precursor salt will then be calcined at elevated temperatures sufficient to decompose the salt to the corresponding high surface area spinel. The unsupported, high surface area Fe-Co spinels prepared in this manner, possess surface areas (BET) in the range of about 100–200 $m^2/g$ (square meters per gram), which are significantly higher than corresponding Fe-Co spinels prepared by conventional processes, e.g., 0.2–1.0 $m^2/g$.

The copper and, if desired, additional promoter metal or metals will then be added to the so-formed Fe-Co spinel by any means known to those skilled in the are such as incipient wetness impregnation or multiple impregnation with one or more promoter metal salt solutions, etc. The choice being left to the conveniece of the practitioner. After the promoter metal or metals have been added to the Fe-Co spinel by surface deposition or impregnation, the catalyst compositions of this invention may be formed by either of the two methods. In one method, the Fe-Co spinel containing copper and, if desired, additional promoter metal, will be charged to the reactor where the catalyst composition will be formed in-situ by contacting with a mixture of $H_2$ and CO at a temperature sufficient to obtain a fully reduced and carbided or carburized composition which is the catalyst of this invention. This may be accomplished under Fischer-Tropsch reaction conditions.

In another, alternative method, the Fe-Co spinel containing copper and, if desired, additional promoter metal will be subjected to high temperature, e.g., 300°–400° C., $H_2$ reduction to obtain a fully reduced alloy, followed by treatment with $H_2$/CO at elevated temperature (i.e., 300°–400° C.) to convert the alloy to a fully carburized state.

The resulting copper promoted, high surface area reduced and carburized or carbided catalysts provide unusually high activity, selectivity and activity maintenance in the direct conversion of CO/$H_2$ to alpha-olefins under slurry reactor conditions. These catalysts have higher CO conversion activity and greater selectivity to alpha-olefins than similar compositions which are not promoted with copper disclosed in copending Ser. Nos. 561,190 and 561,192 filed on Dec. 14, 1983. These catalysts are especially useful in low pressure slurry reactor systems where alpha-olefin residence times in the reaction zone can be minimized, and the physical properties of the catalyst bed are conducive to use of finely divided powdered catalysts.

In accordance with this invention, there is provided a composition of matter comprising an unsupported, iron-cobalt spinel promoted with copper and, if desired, one or more promoter metals of Group IA and IIA, said spinel exhibiting a single phase powder x-ray diffraction pattern substantially isostructural with $Fe_3O_4$, and possessing a BET surface area greater than 5 $m^2/g$ and an iron-cobalt atomic ratio of about 4 to 1 or above. As a practical matter, in most cases the surface area will be at least about 50 $m^2/g$.

Further provided is a composition of matter comprising a copper promoted iron-cobalt metallic alloy, being isostructural with metallic alpha-iron, as determined by X-ray diffractometry, and possessing a BET surface area greater than 5 $m^2/g$, said alloy being produced by contacting the above, described Fe:Co spinel with a reducing atmosphere.

Also provided is a composition of matter comprising a copper promoted, reduced and carbided iron-cobalt alloy, said composition being substantially isostructural with Chi—$Fe_5C_2$ (Hagg carbide), as determined by X-ray diffractometry, and possessing a BET surface area of greater than 5 $m^2/g$, said composition produced by contacting the above-described iron-cobalt alloy with a carbiding atmosphere. A related composition is also provided being isostructural with $Fe_3C$ (cementite) and having a BET surface greater than 5 $m^2/g$.

Furthermore, there is provided a process for producing the copper-promoted, iron-cobalt spinel composition described above comprising the steps of: (a) evaporating a liquid solution comprising a mixture of iron and cobalt salts of at least one alpha-hydroxy aliphatic carboxylic acid, wherein the molar ratio of total moles of said acid to total moles of said iron and cobalt, taken as the free metals, is about 1:1 or above, and wherein the atomic ratio of iron:cobalt, taken as the free metals in said mixture is greater than 2 to 1; yielding an amorphous residue; and (b) calcining said residue at elevated temperature for a time sufficient to yield an iron-cobalt spinel, exhibiting a single phase spinel, isostructural with $Fe_3O_4$, as determined by powder X-ray diffractometry followed by promotirng said so-formed single phase spinel with copper and, if desired, additional promoter metal of Group IA or IIA or mixture thereof.

It addition, there is provided a process for preparing the above-described, copper promoted, iron-cobalt alloy composition of matter comprising contacting the above-described copper promoted, iron-cobalt spinel with a reducing atmosphere under conditions of elevated temperature, pressure and space velocity for a time sufficient to substantially reduce the metal oxides of the spinel.

There is also provided a process for preparing the above-described copper promoted reduced and carbided spinel comprising the step of contacting the above-described copper promoted iron-cobalt metal alloy, with a carbiding atmosphere under conditions of elevated temperature, pressure and space velocity for a time sufficient to substantially carbide said alloy.

There is further provided a process for synthesizing a hydrocarbon mixture containing $C_2$–$C_{20}$ olefins comprising the step of contacting a catalyst composition, comprised of an unsupported, copper promoted, iron cobalt spinel, or mixture of said spinels which initially exhibit a single spinel phase being isostructural with $Fe_3O_4$, as determined by X-ray diffractometry, and possessing an initial BET surface area greater than 5 $m^2/g$ and an Fe:Co atomic ratio of 4:1 or above, said contacting conducted with a mixture of CO and hydrogen under conditions of pressure, space velocity and elevated temperature for a time sufficient to produce said $C_2$–$C_{20}$ olefins.

DESCRIPTION OF THE INVENTION AND PREFERRED EMBODIMENTS

The high surface area iron-cobalt spinels are isostructural with $Fe_3O_4$, as determined by X-ray diffractometry using copper K alpha radiation and exhibit a single spinel phase. By the term "spinel" is meant a crystal structure whose general stoichiometry corresponds to $AB_2O_4$, where A and B can be the same or different cations. Included within this definition is the commonly found spinel, $Mg\ Al_2O_4$. A and B can have the following cationic charge combinations: $A=+2$, $B=+3$, $A=+4$, $B=+2$, or $A=+6$, $B=+1$. Spinels contain an approximately cubic close-packed arrangement of oxygen atoms with $\frac{1}{8}$ of the available tetrahedra. interstices and $\frac{1}{2}$ of the octahedral interstices filled, and can exhibit hundreds of different phases. Further description of the spinel structure can be found in "Structural Inorganic Chemistry" by A. F. Wells, Third Edition, Oxford Press, and the Article "Crystal Chemistry and Some Magnetic Properties of Mixed Metal Oxides with the Spinel Structure" by G. Blasse, Phillips Research Review Supplement, Volume 3, pp 1–30, (1964). By the term "isostructural" is meant crystallizing in the same general structure type in that the arrangement of the atoms remains very similar with only minor changes in unit cell constants, bond energies, and angles. By the term "single spinel phase" is meant one structural and compositional formula, corresponding to a single spinel material into which all of the metal components are incorporated, and exhibiting one characteristic X-ray diffraction pattern.

These spinels possess a BET surface area greater than 5 $m^2/g$ as determined by the well-known BET surface area measurement technique as described in reference JACS Vol. 60, p. 309 (1928) by S. Brunauer, P. H. Emmett, G. Teller, and preferably the spinel has a surface area greater than 50 $m^2/g$ and particularly preferred of about 100 to 300 $m^2/g$. This obtained surface area is in contrast to conventional methods of spinel formation, e.g., high temperature sintering of component oxides in an oxygen-free atmosphere which results in surface areas generally in the range of about 0.1 to 1 $m^2/g$. The high surface area obtained in the present process corresponds to about 0.01 to 0.002 microns in particle size.

The iron to cobalt atomic ratio of the metals in the spinel is 4:1 or above and is preferably in the range of 7:1 to 35:1, and particularly preferred in the range of 19:1 to 20:1. The amount of copper promoter employed will range from about 0.1 to 5 gram atom percent based on the combined iron and cobalt content of the spinel preferably the amount of copper promoter will range from about 0.5 to 2 gram atom %. As set forth above, the copper may be deposited on or added to the spinel by impregnating the spinel with a solution of a suitable copper salt such as copper nitrate, sulfate, halide, acetate, etc.

The spinel can be represented by the formula: $Fe_xCo_yO_4$, wherein x and y are decimal or integer values other than zero, and wherein the sum of x plus y is 3 and the ratio of x to y is 4:1 and preferably being about 7 to 1 to 35 to 1. Particularly preferred is where the iron to cobalt atomic ratio is about 19 to 20 to 1. Illustrative, but non-limiting examples of spinels corresponding to the formula include $Fe_{2.85}Co_{0.15}O_4$, $Fe_{2.625}Co_{0.375}O_4$, $Fe_{2.97}Co_{0.03}O_4$, and $Fe_{2.25}Co_{0.75}O_4$. The composition utilized may comprise a mixture of spinels in which at least two iron-cobalt spinels are present, being isostructural with $Fe_3O_4$, having BET surface areas greater than 5 $m^2/g$, wherein said spinels individually possess different iron-cobalt atomic ratios, being 4:1 or above.

Physical properties, in general, of these spinels are similar to those of magnetite, $Fe_3O_4$, and include: melting point above 1400° and brown to black in color.

Additional promoter metal selected from the group consisting essentially of one or more metals of Group IA and IIA can also be used in the catalyst composition to promote olefin formation in a Fischer-Tropsch process. General classes of suitable promoter agents include carbonates, bicarbonates, organic acid salts, e.g. acetates, inorganic acid salts such as nitrates, halides, sulfates and hydroxides of the Group IA and IIA metals including lithium, sodium, potassium, rubidium, cesium, barium, calcium, strontium, magnesium, and the like. Illustrative, but non-limiting examples of specific promoter agents include potassium carbonate, potassium sulfate, potassium bicarbonate, cesium chloride, rubidium nitrate, lithium acetate, potassium hydroxide, and the like. Preferred are the Group IA compounds potassium carbonate being particularly preferred. These promoters can be added to the iron-cobalt spinel, if desired, simply by impregnating the iron-cobalt spinel composition with an aqueous solution of one or more of said promoter agents and drying the resulting impregnate.

The additional promoter, if used, will generally be present in about a 0.1 to 10 gram-atom % of metal ion based on the total, combined Fe-Co metals gram-atoms. A preferred level of promoter agent is in the range of 1 to 2 gram-atom %. A particularly preferred spinel composition of the subject invention is $Fe_{2.85}Co_{0.15}O_4/1\%$ Cu, 2% K.

In the empirical formulas used herein, the amount of the promoter agent, e.g., potassium, is expressed in terms of gram atom percent based on the total gram-atoms of metals used. Thus, "1 gram-atom percent of potassium" signifies the presence of 1 gram-atom of potassium per 100 total gram atoms of combined gram atoms of Fe and Co.

The copper-promoted spinels undergo unexpectedly facile in-situ reduction in a slurry liquid and pretreatment to form copper-promoted iron-cobalt alloys, which are further in situ carbided to form active slurry catalysts in a Fischer-Tropsch slurry process for making $C_2-C_{20}$ olefins from CO/hydrogen.

The spinels can be made by a process in which an aqueous solution of cobalt and iron salts of an alpha-hydroxy aliphatic carboxylic acid, is evaporated to dryness, leaving an amorphous residue, which is then heated at elevated temperature to substantially form the spinel, as a single spinel phase, being isostructural with $Fe_3O_4$ and possessing a surface area greater than 5 $m^2/g$, preferably above 50 $m^2/g$. The heating is conducted such that no significant loss in surface area of the final spinel is incurred.

The key to the synthesis of these spinels is in the use of an organic, saturated, aliphatic, alpha-hydroxy carboxylic acid to form a complex salt, which is soluble in the aforementioned aqueous medium, at a pH on the acidic side, i.e., pH of 5–7. The solubility of the iron and cobalt organic salts of the alpha-hydroxy carboxylic acid prevent crystallization from occurring, resulting in a crystalline product being obtained from the solution, which would possess a relatively low surface area.

This method of preparation utilizes an alpha-hydroxy aliphatic carboxylic acid which acts as a solubilizing agent for the iron and cobalt salts in the aqueous solution. Any saturated aliphatic alpha-hydroxy carboxylic acid, containing at least one alpha-hydroxy grouping, can be used to form the soluble iron and cobalt salts in the subject invention process in aqueous solution, is deemed to be included within the scope of this invention. Representative examples of such acids which can be mono-hydroxy or di-hydroxy or mono-carboxylic or di-carboxylic are glycolic, malic, glyceric, mandelic, tartaric, lactic acids and mixtures thereof. A preferred carboxylic acid used in the process is glycolic acid.

The amount of acid used is at least the stoichiometric amount, i.e., 1 to 1 molar ratio for each metal present and preferably in about a 5–10% molar excess of the stoichiometric amount. Higher ratios can be used, if it is economical to do so. Lower amounts can also be used but would result in incomplete iron and cobalt acid salt formation.

The first step in the process comprises forming an aqueous solution by dissolving iron salts and cobalt salts, in a water-soluble salt form such as their nitrates, sulfates, chlorides, acetates, and the like, in water.

The concentration of the salts in the aqueous liquid is not critical to the extent that the salts are present in less than a saturated solution to avoid precipitation. For example, an 80–90% saturated solution, of combined dissolved metal molarities for avoiding precipitation in the process, can be effectively used.

The temperature of the aqueous solution is not critical and may be above room temperature to aid in the solubilizing process. However, room temperature is adequate and is the temperature generally used in the process. The pressure also is not critical in the process and atmospheric pressure is generally used.

The aqueous solution can also contain a small amount of organic solvent such as ethanol, acetone, and the like for aiding in the solubilizing of the iron and cobalt salts of the alpha-hydroxy carboxylic acid.

Following the dissolving of the iron and cobalt salts, the alpha-hydroxy carboxylic acid is added, together with a sufficient quantity of base, usually being ammonium hydroxide, sodium hydroxide, potassium hydroxide, and the like, preferably ammonium hydroxide, to solubilize the resulting acid salts. The amount of base added is sufficient to keep the pH in the range of about 5 to 7.0.

It should be noted that the exact sequence of steps need not be adhered to as described above, with the proviso that the resulting aqueous solution contain dissolved iron and cobalt salts in stoichiometric amounts as iron and cobalt salts of alpha-hydroxy carboxylic acid in solution. If there are any insoluble materials present after addition of the base and organic acid, they should be filtered prior to the evaporation step.

At this point, the resulting solution is evaporated, as for example, by air drying, or under reduced pressure, at elevated temperature, as practiced in a rotary evaporator, or in a vacuum drying oven.

The resulting material from the evaporation step is an amorphous residue, generally being a powder. This residue is heated at elevated temperature at 100° to 600° C. for about 1 to 24 hours in generally air to result in a substantially single spinel phase which is isostructural with $Fe_3O_4$, as determined by X-ray diffractometry, as previously described herein. Preferred temperature range is 100°–400° C., and particularly preferred is about 350° C. for single phase spinel formation.

A further subject of the instant invention is a composition of matter comprising a copper promoted, reduced, iron-cobalt metallic alloy formed from the copper-promoted spinel described above, said alloy being isostructural with alpha-iron, as determined by X-ray diffractometry, and preferably possessing a BET surface area of at least about 5 $m^2/g$ or higher.

Generally preferred is where the surface area is about 5–10 $m^2/g$ and particularly preferred being 6–8 $m^2/g$. The atomic ratio of iron to cobalt is not restricted and can be 4:1 and above. Generally, however, for $C_2$–$C_{20}$ olefin synthesis in the subject process described herein, the iron-cobalt atomic ratio is preferably about 4 to 1 and above and more preferably being about 7 to 1 to 35 to 1 and a particularly preferred range is of about 19:1 to 20:1.

The copper-promoted iron-cobalt alloy can be produced by reducing the above-described copperpromoted iron-cobalt spinel in a reducing atmosphere at elevated temperature generally of about 240° C. and above and preferably 300° to 400° C. The reduction can be carried out with various reducing gases including hydrogen, $H_2$/CO, and the like, and mixtures thereof. Preferably hydrogen gas alone is generally used in an inert carrier medium such as helium, neon, argon, or nitrogen, in the absence of CO when substantially pure, non-carbided alloy is desired.

The alloy can be prepared ex situ in a tube reactor or in situ in a Fischer-Tropsch slurry process. The in situ preparation is conducted in the slurry apparatus when the above described copper-promoted spinel is reduced while suspended in the slurry liquid, in a reducing atmosphere being preferably a hydrogen atmosphere at elevated temperature being about 240° C., or above, preferably at 240°–300° C., at a space velocity, pressure, and hydrogen concentration sufficient to cause substantial reduction of the spinel to the alloy. Substantial reduction is complete when the X-ray diffraction pattern shows a pattern substantially isostructural with alpha-iron.

The above-described alloy is useful in forming a carbided, copper-promoted iron-cobalt catalyst useful in the subject Fischer-Tropsch slurry process for making $C_2$–$C_{20}$ olefins, as described herein.

Also, subject of the instant invention are compositions of matter being copper promoted, reduced and carbided iron-cobalt alloys, one being isostructural with $Fe_5C_2$, "Hägg carbide" as described in *Trans. of the Iron & Steel Inst. of Japan*, Vol. 8, p. 265 (1968) by Nagakura et al., as determined by X-ray diffractometry and possessing a BET surface area of greater than 5 $m^2/g$; and two, being isostructural with $Fe_3C$ "cementite", as determined by X-ray diffractometry, and possessing a BET surface area of greater than 5 $m^2/g$.

Preferred is where the surface area of either material is about 25–200 $m^2/g$ and particularly being preferred of about 60–150 $m^2/g$, including both the formed Fe-Co carbide and surface carbon formed during the carbiding step.

The atomic ratio of the iron:cobalt is not restricted for either composition but generally for use in the subject process for producing $C_2$–$C_{20}$ olefins is 4:1 or above and preferably 7:1 to 35:1 and particularly preferred in the range of about 19–20:1.

The copper promoted, carbided iron-cobalt alloy, having an X-ray diffraction pattern isostructural with $Fe_5C_2$, can be produced by carbiding the copper promoted iron-cobalt alloy, described hereinabove, in a suitable carbiding atmosphere at elevated temperature of up to about 400° C. Temperatures above 500° lead to formation of Fe-Co carbides which are isostructural with $Fe_3C$, cementite.

Carbiding atmospheres which can be used to produce the subject reduced, carbided, catalyst include CO, CO/hydrogen, aliphatic hydrocarbons, aromatic hydrocarbons, and the like. A preferred carbiding atmosphere is CO/hydrogen. When using CO/hydrogen carbiding atmosphere, mixtures of CO/hydrogen can be used in a 1:10 to 10:1 molar volume ratio. A preferred ratio used for carbiding purposes is a 1:1 molar ratio.

The carbiding step is generally conducted at a temperature of about 250° C., or above and preferably at 300° to 400° C. A preferred method of carbiding the alloy is in situ in the slurry liquid to be used in the Fischer-Tropsch process. A particularly preferred method is where the spinel is treated with a mixture of CO/hydrogen and reduced and carbided in situ in one step prior to hydrocarbon synthesis. The pressure is generally about 1 atmosphere, and a space velocity of about 20–20,000 v/v/hr is chosen in order to completely carbide the starting iron-cobalt oxide which can be determined by X-ray diffractometry when the material becomes isostructural with Haag carbide, $Fe_5C_2$. The Haag-type Fe-Co carbides produced in this process are of the general formula: $Fe_{5-(5/3)y}Co_{(5/3)y}C_2$, and also include surface carbon produced during the carbiding process. Carbiding temperatures above 500° C. and preferably 500°–700° C., lead to formation of a mixed Fe-Co carbide of the general formula $Fe_{3-y}Co_yC$, which is generally formed under ex situ procedures which allow the use of higher temperatures than possible in the in situ slurry process.

The resulting carbide is an active slurry catalyst for producing $C_2$–$C_{20}$ olefins in the described Fischer-Tropsch slurry process.

If the above-described alloy and carbide, are prepared ex-situ or independently of the slurry apparatus, they may be pyrophoric and inconvenient to handle. In that case, the material may be passivated by contact with oxygen for a sufficient time to reduce or eliminate th pyrophoric tendency. Generally, the oxygen used in the passivating process is used in an inert gas stream carrier such as helium for a sufficient time to cause passivation. Generally, this is conducted preferably at room temperature, at a pressure and space velocity which are convenient and easy to control and to maximize the efficiency of the process needed for complete passivation.

Also, a subject of the instant invention is a Fischer-Tropsch process for producing $C_2$–$C_{20}$ olefins by utilizing the copper promoted iron-cobalt spinel, copper promoted iron-cobalt alloy and the reduced, carbided, copper promoted iron-cobalt spinel catalyst described hereinabove.

Although a fixed bed process can be used, a preferred process mode for operating the Fischer-Tropsch process utilizing the catalysts described herein is a slurry-type process wherein the catalyst in fine particle size and high surface area being above 5 $m^2/g$ is suspended in a liquid hydrocarbon and the CO/hydrogen mixture forced through the catalyst slurry allowing good contact between the CO/hydrogen and the catalyst to initiate and maintain the hydrocarbon synthesis process.

Advantages of a slurry process over that of a fixed bed process are that there is better control of the exothermic heat produced in the Fischer-Tropsch process during the reaction and that better control over catalyst activity maintainance by allowing continuous recycle, recovery, and rejuvenation procedures to be implemented. The slurry process can be operated in a batch or in a continuous cycle, and in the continuous cycle, the entire slurry can be circulated in the system allowing for better control of the primary products residence time in the reaction zone.

The subject process can use any of the above described materials, as catalyst or catalyst precursors: the copper promoted iron-cobalt spinel isostructural with $Fe_3O_4$; the copper promoted iron-cobalt alloy isostructural with alpha-iron; or, the reduced, carbided, copper promoted iron-cobalt alloy which is isostructural with $Fe_5C_2$, or $Fe_3C$. All the materials must have a BET surface area of greater than 5 $m^2/g$, to be applicable in the efficient claimed slurry process described herein. These materials can also be made independently of the apparatus prior to use or can be made in situ in the apparatus during the carrying out of the process. A preferred procedure is where the copper promoted spinel, in high surface area form is pretreated in situ in the slurry liquid, in either distinct reduction-carbiding steps or in one reduction-carbiding step as with CO/hydrogen at elevated temperature. A full discussion of each of the materials, their properties and their preparation are given hereinabove and need not be reiterated.

The slurry liquid used in the process is a liquid at the reaction temperature, must be chemically inert under the reaction conditions and must be relatively good solvent for CO/hydrogen and possess good slurrying and dispersing properties for the finely divided catalyst. Representative classes of organic liquids which can be utilized are high boiling paraffins, aromatic hydrocarbons, ethers, amines, or mixtures thereof. The high boiling paraffins include $C_{10}-C_{50}$ linear or branched parafinnic hydrocarbons; the aromatic hydrocarbons include $C_2-C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. The slurry liquid can contain N and O in the molecular structure but not S, P, As or Sb, since these are poisons in the slurry process. Representative examples of specific liquid slurry solvents useful are dodecane, tetradecane, hexadecane, octadecane, cosane, tetracosane, octacosane, tetratetracontane, toluene, o-, m-, and p-xylene, mesitylene, $C_1-C_{12}$ mono- and multi-alkyl substituted benzenes, dodecylbenzene, naphthalene, anthracene, biphenyl, diphenylether, dodecylamine, dinonylamine, trioctylamine, and the like. Preferred liquid hydrocarbon slurry solvent is octacosane or hexadecane.

The amount of catalyst used in the liquid hydrocarbon slurry solvent is generally about 10 to 60 g. of dry catalyst per 500 g. slurry liquid. Preferably about 30 to 50 g. dry catalyst per 500 g. slurry liquid slurry is utilized, being in about a respective 5:1 to 10:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases. In a typical laboratory unit the rate of stirring is generally carried out in the range of about 600 to 1,200 rpm and preferably 1,000 to 1,200 rpm.

Prior to the CO/hydrogen hydrocarbon synthesis run, the reduced and carbided, copper promoted iron-cobalt catalyst is generally conditioned in the apparatus by purging with nitrogen to remove reactive oxygen-containing gases and then the temperature is increased while stirring to the reaction temperature range. Then the system is generally subjected to a hydrogen treatment for a sufficient time to insure complete removal of any surface metal oxide present which would interfere in hydrocarbon synthesis.

Optionally, and preferably if the catalyst is prepared in situ, then the hydrogen treatment is generally not required or is only practiced for a short period of time. The pressure and space velocity during the inert gas-hydrogen conditioning step are not critical and can be utilized in the range which is actually used during actual hydrocarbon synthesis.

Following the conditioning step, the CO/hydrogen feedstream is introduced into the slurry catalyst chamber and the pressure, space velocity, temperature, and hydrogen/CO molar ratio is then adjusted, as desired, for hydrocarbon synthesis conditions.

In the process, the hydrogen and CO are used in a molar ratio in the gaseous feedstream in about a 10:1 to 1:10 molar ratio, preferably 3:1 to 0.5:1, and particularly preferred 1:1 to 2:1 molar ratio.

The temperature in the process is generally in the range of about 200° to 300° C., preferably being 230° to 270° C., and particularly preferred of about 240°–260° C. Higher temperature ranges can also be used but tend to lead to lighter products and more methane, lower temperature ranges can also be used but tend to lead to lower activity and wax formation.

The pressure useful in the process is generally conducted in the range of about 50 to 400 psig and preferably about 70 to 225 psig. Higher pressures can also be used but tend to lead to waxy materials particularly in combination with lower temperature.

The space velocity used in the process is generally about 100 to 4,000 volumes of gaseous feedstream/per volume of dry catalyst in the slurry/per hour and is preferably in the range of about 400 to 1,200 v/v/hr, and particularly preferred of 800–1,200 v/v/hr. Higher space velocities can also be used but tend to lead to lower % CO conversion, and lower space velocities can also be used but tend to lead to more paraffinic products.

Generally, after the pretreatment, the CO/hydrogen feedstream is introduced to initiate and maintain hydrocarbon synthesis.

The percent CO conversion obtainable in the subject process, while providing substantial quantities of $C_2$–$C_{20}$ olefins, will generally range from about 30 to 80 percent and usually from about 50 to 60 percent for sufficient $C_2$–$C_{20}$ olefin production.

"Total hydrocarbons" produced in the process is related to the selectivity of percent CO conversion to hydrocarbons being those hydrocarbons from $C_1$ to about $C_{40}$ inclusive. Total hydrocarbon selectivity is generally 0 to 50 percent and higher, of the total CO converted, and the remainder converted to $CO_2$.

The percent $C_2$–$C_{20}$ hydrocarbons of the total hydrocarbons produced including methane and above is about 60 to 90 wt. %. The percent of $C_2$–$C_{20}$ olefins produced, of the $C_2$–$C_{20}$ total hydrocarbons produced is about 60 to 70 wt. %. The olefins produced in the process are substantially alpha olefins.

The selectivity to methane based on the amount of CO conversion is about 1 to 10 weight percent of total hydrocarbons, produced. Preferably about 5 percent, and lower, methane is produced in the process.

As discussed above, the percent selectivity to $CO_2$ formation in the process is about 10 to 50 percent of CO converted.

Preferably, the reaction process variables are adjusted to minimize $CO_2$ production, minimize methane production, maximize percent CO conversion, and maximize percent $C_2$–$C_{20}$ olefin selectivity, while achieving activity maintenance in the catalyst system.

Generally, this format can be derived in a preferred mode of operating the process where the slurry liquid used is hexadecane, the catalyst used is $Fe_{2.85}Co_{0.15}O_4$/1%Cu, 2% K, the catalyst/liqud weight ratio is 40/500, the system is stirred at 1,200 rpm, and pretreatment procedure is conducted in situ in a one step procedure using 9:1$H_2$/$N_2$ at 220° C., atmospheric pressure, 1200 v/v/hr. space velocity, for a period of 5 hrs., and the process conducted at the hydrogen:CO molar ratio is 1:1, the temperature is conducted at about 245° C., at a pressure of 7–150 psig, and space velocity 1,000–1200 v/v/hr. By carrying out the above process in the stated variable ranges efficient activity maintenance and production of $C_2$–$C_{20}$ olefins can be achieved.

The effluent gases in the process exiting from the reactor may be recycled if desired to the reactor for further CO hydrocarbon synthesis.

Methods for collecting the products in the process are known in the art and include fractional distillation, and the like. Methods for analyzing the product liquid hydrocarbons and gaseous streams are also known in the art and generally include gas chromatography and the like.

Apparatus useful in the preferred process is any conventional slurry-type reactor, being horizontal or vertical, being stationary or cyclical, in catalyst slurry. Other apparatus not specifically described herein will be obvious to one skilled in the art from a reading of this disclosure.

The invention will be more readily understood by reference to the examples below.

EXAMPLES

Unless otherwise indicated, the selectivity weight percentages of product hydrocarbons is given on a $CO_2$-free basis.

EXAMPLE 1

Preparation of $Fe_{2.85}Co_{0.15}O_4$ Spinel 198.04 grams of ferric nitrate in 144 cc of water and 7.5 grams of cobalt nitrate in 8 cc of water were mixed together. To this solution was added a solution of 41.6 grams of 85% glycolic acid containing 45 cc of ammonium hydroxide such that the resulting pH of the ammonium glycolate solution was about 6.5. The ammonium glycolate solution constituted 0.51 moles of glycolic acid such that about a one to one molar ratio of total metals including iron and cobalt to glycolic acid resulted. The ammonium glycolate solution was added to the aqueous solution containing iron and cobalt salts and the contents stirred. The resulting solution was allowed to evaporate by air drying. Upon drying at room temperature the resulting solid was shown by X-ray diffraction to be an amorphous material because of lack of sharp discrete reflections. The solid was heated in air at 350° C. for 2 hours. An X-ray diffraction pattern of the resulting material showed it to be a single phase cobalt-iron spinel isomorphous with $Fe_3O_4$. The X-ray diffraction peaks were broadened relative to a compositionally equivalent material obtained by a high temperature procedure. This indicated that the resulting obtained material was of very small particle size.

A number of different batches of this spinel were prepared using the procedure set forth above. In all cases, the surface area of the resulting material ranged from about 80 to 200 square meters per gram.

Preparation of $Fe_3O_4$

For comparative purposes, $Fe_3O_4$ was prepared from ferric nitrate, glycolic acid and ammonium hydroxide using the procedure set forth above for the $Fe_{2.85}Co_{0.15}O_4$ spinel, except that no cobalt salt was employed.

Impregnation With Promoter

Samples of the spinel and $Fe_3O_4$ prepared as set forth above were impregnated with either potassium or a mixture of potassium and copper. For the copper impregnation, an aqueous solution of cupric nitrate hexahydrate was used in an amount sufficient to deposit one gram atom % of Cu on the spinel, based on the combined Fe and Co content. The resulting copper impregnate was then dried in air for about two hours at 125° C.

Following the Cu impregnation, samples of the dried impregnate were further impregnated with one gram atomic percent of potassium using an aqueous solution of potassium carbonate followed by drying of the resulting impregnated sample at 125° C. Some samples were impregnated only with K. Resulting solid had an empirical formula of $Fe_{2.85}Co_{0.15}O_4$/1% K.

Preparation of Carbide Ex-Situ

In those cases where the catalyst was prepared ex-situ, the promoted iron or iron-cobalt spinel was treated at 400° C. in a stream of 40 volume percent hydrogen/40% helium/20% CO at 200 V/V/hr. for twentyfour hours. Following this, the sample was cooled to room temperature and 1.0% oxygen in helium was introduced for one hour to passivate the material. The X-ray diffraction pattern of the resulting material was isostructural with $Fe_5C_2$. The BET nitrogen surface area of the material was at least about 150 m$^2$/g. Analysis showed that about 40–50 weight percent of the material was carbon and thus the material was a composite of $Fe_{5-x}Co_xC_2/2$ gram-atom % K, and, in some cases, 1 % Cu and surface carbon. In this case x=0 or 0.25.

Catalyst Runs

Into a slurry reactor, being a 300 cc Parr CSTR (continuous stirred tank reactor) was charged: 50 g of octacosane and 8.0 of either the ex-situ carbided catalyst or the Cu and/or K promoted Fe or Fe-Co spinel prepared as set forth above. In those cases where the reactor was charged with a promoted spinel that had not been carbided ex-situ, the catalyst was formed in-situ in the reactor.

After a sample of catalyst or promoted spinel catalyst precursor was loaded into the reactor, the system was purged with nitrogen and then placed under CO hydrogenation reaction conditions by adjusting the reaction temperature to 270° C., the $H_2/CO$ volume ratio to 2/1, the space velocity to 2,000 V gaseous feedstream/V dry catalyst/hr, the pressure to 75 psig, and the slurry stirrer speed to 600 rpm in the octacosane solvent.

The actual gas flow rate through the reactor was 120/60/20 cc per min. of $H_2/CO/N_2$. The effluent gas from the reactor was monitored by an HP-5840A Refinery Gas analyzer to determine percent CO conversion and the nature of the hydrocarbon products.

The results are set forth in Tables 1 and 2 below. In all cases, the values reported were determined after the catalyst had been on-stream in the reactor for a period of at least 16 hours.

Referring to the Tables, Table 1 sets forth the results of three different catalysts formed in-situ in the reactor from the promoted Fe or Fe/Co spinel. The results show the high selectivity of α-olefin production achieved by the copper promoted catalyst of this invention compared to a similar catalyst which was not promoted with copper. The data for the Fe spinel merely serves as a comparison for conventional iron catalysts. Table 2 compares the result obtained using a catalyst of this invention prepared both in-situ and ex-situ. These data illustrate that the catalysts of this invention are preferably prepared in-situ for greatest alpha olefin selectivity.

TABLE I

| Catalysts Prepared In-Situ in The Reactor | | | |
|---|---|---|---|
| | $Fe_3O_4/$ 2% K[a] | $Fe_{2.85}Co_{15}O_4/$ 2% K | $Fe_{2.85}Co_{.15}O_4/$ 2% K/1% Cu |
| % CO conversion | 67 | 77 | 86 |
| % $CH_4$ make | 2.02 | 4.4 | 4.2 |
| % olefins in $C_2$-$C_4$ hydrocarbon fraction | 47.5 | 91 | 87 |
| $C_{10}$ distribution | | | |
| α - olefins | | 49.0 | 59 |
| n - paraffins | | 14.9 | 15 |
| η - alcohols | | 1.0 | 3 |
| β - olefins | | 4.1 | 2 |
| All Else | | 31 | 21 |

Note
[a] No measurable amount of $C_{10}$'s produced with this catalyst.

TABLE 2

| Catalysts Prepared In-Situ and Ex-Situ | | | |
|---|---|---|---|
| | $Fe_3O_4/$ 2% K ex-situ | $Fe_{2.85}Co_{.15}O_4/$ 1% CU, 2% K ex-situ | $Fe_{2.85}CO_{.15}O_4/$ 1% Cu, 2% K in-situ |
| % CO conversion | 49 | 54 | 86 |
| % $CH_4$ make | 3.8 | 4.5 | 4.2 |
| % olefins produced in $C_2$-$C_4$ hydrocarbon fraction | 77 | 85 | 87 |
| $C_{10}$ distribution | | | |
| α - olefins | 50 | 46 | 59 |
| β - olefins | 8 | 6.0 | 2 |
| η - alcohols | 2 | 1 | 3 |
| n - paraffins | 17 | 18 | 15 |
| All Else | 23 | 29 | 21 |

What is claimed is:

1. A process for synthesizing a hydrocarbon mixture containing $C_2$-$C_{20}$ olefins comprising contacting a catalyst composition, comprising an unsupported, copper promoted iron-cobalt spinel, said spinel exhibiting a single phase being isostructural with $Fe_3O_4$ as determined by powder X-ray diffractometry, and possessing an initial BET surface area greater than 5 $m^2/g$ and an Fe:Co atomic ratio of 4:1 and above, with a mixture of CO and hydrogen in a slurry liquid under conditions of pressure, space velocity, and elevated temperature, for a time sufficient to produce said $C_2$-$C_{20}$ olefins.

2. The process of claim 1 wherein said slurry liquid is selected from high boiling liquid paraffins, aromatic hydrocarbons, ethers, amines, or mixtures thereof 3. The process of claim 2 wherein said high boiling liquid paraffins are $C_{12}$-$C_{60}$ linear or branched saturated aliphatic hydrocarbons.

4. The process of claim 3 wherein said hydrocarbon slurry liquid is selected from octacosane, hexadecane, or mixtures thereof.

5. The process of claim 1 wherein said hydrogen and CO are present in a hydrogen/CO molar ratio of 1:10 to 10:1.

6. The process of claim 1 wherein said temperature is in the range of about 200° to 300° C.

7. The process of claim 1 wherein said pressure is in the range of about 50 to 250 psig.

8. The process of claim 1 wherein said space velocity is in the range of about 100 to 4000 v/v/hr.

9. The process of claim 1 wherein the weight ratio of slurry liquid to dry catalyst is in the range of about 10:1 to 5:1.

10. The process of claim 1 wherein said copper promoted spinel is reduced and carbided in situ in the process in the slurry liquid.

11. The process of claim 1 wherein the catalyst is reduced and carbided ex situ.

12. The process of claim 1 wherein said carbided, reduced, copper promoted spinel is isostructural with $Fe_5C_2$, or $Fe_3C$, as determined by powder X-ray diffractometry.

13. The process of claim 1 wherein said iron and cobalt are present in an iron-cobalt atomic ratio of 4:1 or above and wherein said copper is present in an amount of from about 0.1 to 5 gram atom % of the iron and cobalt.

14. The process of claim 13 wherein said atomic iron-cobalt ratio is 7:1 to 35:1.

15. The process of claim 14 wherein said iron-cobalt atomic ratio is 19-20:1.

16. The process of claim 1 wherein said spinel has an initial BET surface area of at least about 50 $m^2/g$.

17. The process of claim 16 wherein said spinel has a BET surface area of from about 70 to 220 m²/g.

18. The process of claim 1 wherein said catalyst composition further comprises a Group IA and IIA promoter agent present in about 0.1 to 10 gram-atom percent of said total gram-atoms of metals content.

19. The process of claim 18 wherein said promoter agent is selected from the group of carbonate, bicarbonate, organic acid salts, inorganic acid salts, nitrate, halide, sulfate, and hydroxides of Group IA and IIA metals.

20. The process of claim 19 wherein additional said promoter agent is potassium carbonate.

21. The process of claim 1 wherein said spinel catalyst composition is $Fe_{2.85}Co_{0.15}O_4$ with 2 gram-atom % K and 1 gram atom % Cu.

22. The process of claim 1 wherein said product hydrocarbon mixture contains 60 wt.% $C_2$–$C_{20}$ olefins.

23. The process of claim 1 wherein said hydrocarbon mixture contains a $C_2/C_{20}$ paraffins and olefins in an olefins/paraffins weight ratio of 3:1.

* * * * *